| United States Patent [19] | [11] | 4,247,575 |
|---|---|---|
| O'Connell et al. | [45] | Jan. 27, 1981 |

[54] METHOD OF SILVER PLATING A TOOTH STRUCTURE

[75] Inventors: John J. O'Connell; William R. Pike, both of Tustin, Calif.

[73] Assignee: American Hospital Supply Corporation, Evanston, Ill.

[21] Appl. No.: 89,182

[22] Filed: Oct. 29, 1979

[51] Int. Cl.$^3$ ............................ A61K 5/02; C23L 3/02
[52] U.S. Cl. ................................ 427/2; 204/157.1 R; 433/202; 106/35
[58] Field of Search ................. 433/202; 204/157.1 R; 427/2, 4, 53.1; 106/35

[56] References Cited

U.S. PATENT DOCUMENTS

| 3,562,005 | 2/1971 | Angelo | 204/157.1 |
|---|---|---|---|
| 3,943,267 | 3/1976 | Randol | 427/2 |
| 3,995,371 | 12/1976 | O'Keefe | 427/2 |
| 4,181,757 | 1/1980 | Youdelis | 427/2 |

*Primary Examiner*—Sam Silverberg
*Attorney, Agent, or Firm*—Tilton, Fallon, Lungmus & Chestnut

[57] ABSTRACT

An improved method for securing a thin continuous layer of metallic silver upon a tooth structure, especially the dentin surface of that structure, to seal the surface and, where desired, to provide a highly receptive surface for an amalgam restoration. The method involves first coating the dentin surface with an aqueous solution of a silver salt to form a silver-protein complex, then photoreducing the silver of that complex to produce a black base layer of complexed metallic silver, and thereafter electrolessly plating a continuous silver sealing layer onto the base layer.

13 Claims, No Drawings

METHOD OF SILVER PLATING A TOOTH STRUCTURE

BACKGROUND

O'Keefe U.S. Pat. No. 3,995,371 describes an electroless plating method for applying a thin continuous layer of a metal such as silver upon a tooth surface. The purpose is to seal that surface with a highly adherent layer of metal, thereby providing a more effective substrate for amalgam and other dental restorative materials.

The patented procedure involves the steps of etching an enamel surface and then coating that surface with a plating mixture containing a water soluble metal salt (such as silver nitrate or silver fluoride) and a reducing agent for the metal ions of that salt. The plating mixture is maintained in contact with the enamel surface for several minutes until a continuous shiny layer of metallic silver is deposited on that surface.

Unfortunately, the patented process has a significant limitation. As acknowledged by the patentee (column 6, line 63, to column 7, line 13), the process is effective only for coating enamel; it is not effective for coating predentin (dentin) which, in contrast to enamel, has a large proportion of organic matter. Where a dental excavation extends through the enamel of a tooth into the dentin, a common situation, the patented process can be used only to provide a continuous metallic coating about the edges or rim of the excavation.

The significance of that shortcoming becomes apparent when it is considered that one major advantage of the patented procedure is to provide a secure attachment for an amalgam restoration without the extensive undercutting commonly required within an excavation in order to obtain secure mechanical attachment of the amalgam filling. In those cases where the excavation exposes a substantial area of dentin, the dentist must proceed to enlarge the excavation, providing undercut recesses in the conventional manner, in order to insure secure attachment of the filling.

For the same reasons, the patented process would appear inapplicable in certain prosthodontic procedures such as overdenture preparation. For example, if an endodontically treated tooth is severed at the gum line with the root remaining in place to provide support for a denture and to prevent resorption of bone that might otherwise occur if the root were removed, the patent disclosure makes it clear that some other process must be used to seal the exposed surface of the tooth since no appreciable enamel areas would remain, such surface consisting almost entirely of dentin.

SUMMARY

A main aspect of this invention lies in the recognition that the metal plating process of the aforementioned patent could be useful in plating dentin surfaces, in contrast to enamel surfaces, if a precoating of the same metal were first securely bonded to the proteinaceous content of the dentin, and in the further recognition that photoreduction of silver ions in intimate association with such proteinaceous material would result in the formation of a silver-protein complex that could provide a suitable base layer for subsequent electroless plating.

It is an object of this invention to provide an improved method of plating a tooth structure which overcomes the aforementioned shortcomings and disadvantages of the prior art. Specifically, it is an object of this invention to provide a relatively simple and highly effective process for plating metallic silver onto dentin and other rigid proteinaceous substrates to provide a tenacious and impervious coating thereon. A further object is to provide a method for treating a dentin surface in a manner that not only insures a secure bonding of a subsequent silver plating layer but also catalyzes the chemical formation of that layer. A still further object is to provide a method for treating a dentin surface to promote a secure bonding of amalgam to that surface.

In brief, the method of this invention involves the steps of coating a dentin surface with an aqueous solution of a silver salt to produce a silver-protein complex upon that surface, then photoreducing the silver of the complex to produce a black discontinuous base layer of complexed metallic silver secured to that surface, and then electrolessly plating a continuous silver seating layer upon the base layer by utilizing the silver of the silver-protein complex to catalyze chemical reduction of the silver ions of the plating solution. In the embodiment disclosed, the process also includes the additional steps of acid etching the dentin surface prior to the coating step, and of subsequently applying and adhering a restorative material to the continuous silver layer plated on the dentin surface.

Other features, advantages, and objects of the invention will become apparent from the detailed description.

DETAILED DESCRIPTION OF PREFERRED EMBODIMENT

Electroless plating onto a tooth surface is disclosed in considerable detail in the aforementioned patent, and the disclosure of that patent is incorporated by reference herein. The method of this invention expands the usefulness of such electroless plating by providing a way in which a continuous conductive layer of metallic silver may be secured to dentin which, in contrast to enamel, contains a relatively high percentage of protein in the form of collagen.

Since dentin also contains some hydroxy apatite, although to a considerably lesser extent than enamel (approximately 67% for dentin vs. 95% for enamel), it is desirable to acid-treat the dentin surface in order to dissolve apatite near the surface and thereby expose increased amounts of collagen which are not affected by the acid. While the treatment might take place at the same time the base coating is formed or applied, it is believed more effective to carry out the acid etching procedure in a separate preliminary step.

While other etchants might be used, such as strong nitric acid solutions, particularly effective results have been obtained using aqueous phosphoric acid solutions having an acid strength between 20 to 60% by weight. Following such etching, the dentin surface should be washed with water to remove residual acid, thereby avoiding the formation of excessive silver phosphate that might be left unbonded to the dentin in the next step, and protecting the puepal tissue from contact with acid that might otherwise become absorbed by and transmitted through the dentin.

Thereafter, the washed dentin surface is coated with an aqueous solution of a relatively non-toxic silver salt. The aqueous coating may be applied to the dentin substrate in any convenient manner, as by spraying, swabbing, or brushing. The salt solution should be at least 0.25 molar in silver ions and should have a pH less than about 6.0, a pH of 2.0 or less being preferred. Solutions in the pH range of approximately 0.5 to 1.5 have been found particularly effective. While any of a number of silver salts might be useful in carrying out the process of this invention, including silver ammonium nitrate and silver fluoride, silver nitrate is preferred because of its effectiveness and availability. Aqueous solutions containing silver nitrate within the range of 5 to 70% by weight are believed effective, although particularly effective results have been obtained with solutions of 10 to 60%.

Photoreduction of the silver ions is obtained by exposing the coated dentin surface to light in the visible, infrared, or ultraviolet range for an interval sufficient to cause a homogenous blackening of the coated surface. Effective results have been obtained using high intensity light transmitted from a conventional visible light source of the type used for fiber optic dental illumination, as well as from a standard ultraviolet light source. The intervals of exposure should be less than five minutes for reasons of convenience, and preferably less than two minutes, such duration being controlled by selecting a light source of sufficient intensity to promote rapid photoreduction.

While the precise mechanism is not fully known, it is believed that upon contact with the proteinaceous substrate, the silver ions react to form a silver-protein complex on the dentin surface and that exposure to light then reduces the silver without destroying the complex. The result is that submicron sized particles of metallic silver, so small as to appear black, are tenaciously held on the dentin surface. The process is similar to what has long been known to occur in photography where light-sensitive chemical constituents produce images by silver deposition after being exposed to light. Although appearing homogenous or continuous, the black base is actually discontinuous and electrically non-conductive.

More specifically, it is postulated that in the coating and photoreduction steps the following reactions take place:

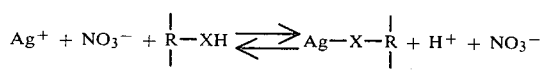

(1)

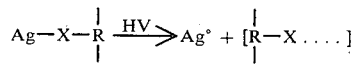

(2)

where

is the complexing group of an amino acid portion of a protein molecule, and

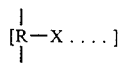

is the corresponding oxidation product. In reaction (1), it is believed that the silver ion forms a complex with the amino acid portion of the protein, thus converting the silver to a state in which it is not only securely bonded to the protein by reason of the silver-protein complex, but one in which it is also easily photoreduced, in contrast to silver which is not so complexed. In the subsequent photoreduction step (2), the highly-dispersed silver complex is then easily reduced to a neutral black-appearing state, presumably because of the ease with which the protein group is oxidized. Although reduced to a metallic state, the silver remains tenaciously bonded to the protein-containing substrate, indicating that the silver-protein complex remains generally intact notwithstanding the oxidation/reduction that has occurred.

Thereafter, the discontinuous black layer of highly-dispersed photoreduced silver is electrolessly plated as generally described in the aforementioned patent, with the qualification that the chemical reduction of the additional silver coating is catalyzed by the photoreduced silver already present on and securely bonded to the dentin surface. The plating procedure produces a continuous, homogenous tightly-adhered, bright silver coating upon the dentin of the tooth structure. As brought out in the aforementioned patent, the continuity of that layer may be increased by successive plating steps. The final result is a sealed tooth surface in which the bright, continuous (electrically conductive) sealing layer is bonded to the discontinuous black base layer because of the silver phase common in both, and because the complexed silver of the base layer provides an in situ catalyst for the chemical reduction of the silver of the sealing layer, and in which the base layer is securely bonded to the protein structure of the tooth.

Any suitable water-soluble salt of silver may be used in carrying out the plating step, all as brought out in the referenced patent, although silver nitrate or silver fluoride are believed particularly effective. The reducing agent may be incorporated in this salt solution, or may be applied in sequence with the salt solution, to provide the aqueous mixture with which the pre-coated substrate is contacted to effect the plating reaction. Any of a number of reducing agents might be used, as brought out in the patent, although ferrous sulfate or ferrous ammonium sulfate [Fe(NH$_4$)$_2$(SO$_4$)$_2$] are deemed especially suitable because of their greater biological compatability.

Once the continuous metallic sealing layer has been plated upon the base layer, a further layer of another more nobel metal can be applied over the sealing layer by cementation, as described in the referenced patent. Since the metal of the subsequent layer will have a lower oxidation potential than the metal of the sealing layer, the sealing metal (silver) will be oxidized and displaced from the surface, and ions of the cementation solution will be concomitantly reduced to the elemental state so that the more nobel metal will be deposited on the surface. Gold, platinum, or palladium may thus be plated over silver.

The method of this invention is especially suitable for the sealing of a dentin surface prior to certain prosthodontic procedures such as overdenture preparation. A tooth, severed at the gum line and endodontically treated, is acid etched, then washed and coated with an aqueous solution of silver nitrate or other silver salt to produce a silver-protein complex upon the exposed dentin surface, then the silver of the complex is photoreduced to form the blackened discontinuous base layer, and finally the base layer is electrolessly plated to form a continuous sealing layer which fully protects the treated surface against fluid invasion. Consequently, the root with its sealed surface provides an ideal natural base structure or foundation for an overdenture.

It is also believed apparent that the method of this invention is particularly useful as an operation preliminary to the attachment of a dental amalgam filling. The sealing layer of continuous silver is strongly adherent to the silver-containing amalgam subsequently applied and, since the sealing layer is also bonded to the dentin by reason of the photoreduced base layer, the chain of attachment from the dentin to the amalgam is complete.

While this invention is particularly concerned with a method for applying a continuous silver sealing layer, with or without a subsequent amalgam restoration, to dentin, it is believed apparent that the described method may be combined with the procedure described in the referenced patent to treat enamel as well as dentin. For example, in preparing a tooth for dental restoration, an excavation which enters the dentin may first be formed in order to remove the caries-affected portion of the tooth. Thereafter, the excavation into the dentin, as well as immediately surrounding areas of enamel, may be acid etched. Following the procedure already described, the excavation is coated with an aqueous solution of silver nitrate or other suitable silver salt, and the silver ion of that solution forms a complex with the protein of the dentin. Thereafter, the complexed silver is photoreduced, forming a deep black layer on the dentin (but not the etched enamel) surface. Finally, the base-coated dentin and the etched peripheral area of the enamel is electrolessly plated, and the amalgam filling is secured in place. Such a procedure not only results in a secure bond between the amalgam and the dentin but, in addition, the amalgam also attaches to the etched and plated areas of enamel surrounding the excavation.

The chemically-bonded continuous silver layer provides a surface which reacts with amalgam to produce an integral, adhesive seal at the tooth/restoration interface. The elimination of a distinct phase boundary at this interface serves to prevent marginal leakage, corrosion, and the deterioration of the restoration associated with these conditions.

The following examples further illustrate the invention.

EXAMPLE 1

A group of 16 freshly extracted teeth were cut to remove crowns therefrom and expose maximal planar surfaces composed primarily of dentin. The surfaces were washed and then while still wet (to prevent shrinkage of dentin) were treated as follows:

| Samples | Etchant | Treatment Solution | Photoreduction Time |
|---|---|---|---|
| 1-4 | None | 20% AgNO$_3$ @ pH 2 | 3 minutes |
| 5-8 | H$_3$PO$_4$ | Same | 1 minute |
| 9-12 | None | Same | 1 minute |
| 13-16 | None | Same (but further acidified with HNO$_3$ to pH 1) | 1 minute |

The phosphoric acid etchant solution was 37% and the etching procedure, where used, involved depositing a drop of the H$_3$PO$_4$ solution to the surface and allowing it to remain there for one minute at room temperature. Following etching, the teeth were rinsed for 10 seconds with running tap water and then blown dry for 10 seconds with oil-free compressed air.

The etched and unetched samples were then exposed to the silver nitrate solution which was prepared by dissolving 20.0 gms AgNO$_3$ in 80.0 gms distilled H$_2$O, with adjustment to a pH of about 1.0 by incremental addition of 10% HNO$_3$ while monitoring pH with a Beckman Zeromatic pH meter. The silver nitrate solution was applied by brushing, using a nylon bristle brush, directly to the dentin surfaces and, after an interval of about 15 seconds, the coated surfaces were exposed to incandescent light emitted from a fiber optic cable connected to a conventional high intensity light source (Model 39D-1010 manufactured by Heyer-Schulte, division of American Hospital Supply Corporation, Evanston, Illinois).

The results revealed that samples 1-4 exhibited an uneven black silver plated surface, samples 5-8 were very black and very homogeneously coated, samples 9-12 had the worst coatings with respect to each of darkness and unevenness, and samples 13-16 were almost identical to samples 5-8.

EXAMPLE 2

The teeth described in Example 1 were thereafter plated by an electroless chemical reduction method in accordance with O'Keefe U.S. Pat. No. 3,995,371. The 16 sample teeth were maintained at room temperature in distilled water after photoreduction until each was individually treated as follows:

Immediately prior to the chemical plating procedure the sample tooth was removed from the distilled water and blown dry with oil-free, compressed air for 15 seconds. A 20% (by weight) aqueous solution of silver nitrate was applied to the surface using a nylon bristle brush. After an interval of 5-10 seconds (enough time to rinse the brush in distilled water and blot dry with a paper towel), a saturated solution of ferrous sulfate (FeSO$_4$.7H$_2$O), prepared by dissolving 50 gms of FeSO$_4$.7H$_2$O in 50 gms of distilled H$_2$O which had been boiled to remove dissolved oxygen and adjusting the pH within the range of 2 to 3 with concentrated H$_2$SO$_4$, was applied to the surface in the same manner as the AgNO$_3$ solution. As the brush containing the ferrous sulfate solution was applied to the surface using a painting motion, metallic silver could be seen depositing on specific areas of the tooth structure surface. The electroless chemical plating process is thus accompanied by alternate applications of silver nitrate solution and ferrous sulfate solution as described above for a total of 5 treatments. After the fifth plating treatment the teeth samples were rinsed with tap water and blown dry with oil-free compressed air for 15 seconds.

The results revealed that where a dark black silver layer had been achieved by photoreduction a gray, even, electrically-conductive metallic silver coating had been deposited on the dentin surface. By contrast, dentin areas which had little or faintly black silver layers, produced uneven, non-conductive metallic silver deposits. Areas which had no black photoreduced silver coating did not plate by the electroless chemical process.

It was also observed that with samples which plated well by this combination of procedures, the heavy gray silver layer could be burnished by wiping the surface with a cotton tipped swab. This burnishing process removed any excess unadhered silver to produce a bright, lustrous metallic silver surface.

EXAMPLE 3

In order to determine the ability of silver plated tooth structure to form strong physico-chemical adhesive bonds to dental amalgam alloy restorative materials, the following experiment was performed:

A group of 12 freshly-extracted human molars were encapsulated into 9/16 inch diameter cylinders using acrylic cold-curing denture base resin. This was accomplished by aligning the tooth in the center of a cylindrical metal mold cavity and pouring the acrylic potting compound (mixed according to manufacturer's directions) over the tooth until only the cusps were exposed. Allowing the potting compound to cure thus encapsulated each tooth with the long axis of the tooth centered with respect to the height of the cylinder and as nearly perpendicular to the diameter as possible.

The potted tooth specimens were then removed from the molds and ground using 180 grit silicon carbide abrasive paper on a polishing wheel to remove the crowns and expose maximal planar surfaces composed primarily of dentin. Final polishing was accomplished using 600 grit paper to provide a flat smooth surface perpendicular to the long axis of the tooth. Immediately after polishing, all specimens were stored in distilled water until further treatment. Thus prepared, the potted specimens were divided into three groups to be treated as follows:

Group A

Four samples were removed from distilled water and etched with 37% phosphoric acid as described in Example 1. After etching, washing and drying using compressed air, each sample was returned to its metal mold, covered with a Teflon ring ¼ inches thick and 9/16 inches in diameter with a 3/16 inch diameter hole in the center.

After securing the Teflon ring (which was split through the diameter to facilitate removal) flush to the exposed etched dentin surface, a dental amalgam alloy restorative material (Oralloy) was mixed according to manufacturers instructions and condensed into the cavity in the center of the Teflon ring. The condensed amalgam alloy hardened in 5 minutes in the form of a 3/15 inch diameter cylindrical plug whose lower surface was in intimate contact with the exposed dentin surface. Ten minutes after the initial mixing of the amalgam alloy the samples, still securely fastened in the mold with split ring in place were transferred to a container of distilled water, totally immersed and maintained at 37° C. until further testing was commenced.

Group B

Four specimens were removed from the distilled water and acid etched using 37% phosphoric acid as described in Example 1. Immediately after etching, washing and drying, the samples were individually coated with 20% aqueous silver nitrate solution (as in Example 1) and exposed to high intensity visible light for one minute to produce a black photoreduced silver layer on the dentin surface. The samples were then rinsed with tap water and blown dry. These samples were then placed in the same type of mold equipped with a Teflon split ring insert, as described for Group A samples. Dental amalgam was condensed as described into cylindrical plugs onto the silver-plated surfaces and the samples were stored in then distilled water at 37° C. for further testing.

Group C

Four samples were prepared identically to those in Group B except that after the photoreduced layer was formed on each sample, a chemically reduced metallic silver layer was then applied by sequential application of 20% aqueous silver nitrate and saturated ferrous sulfate solution as described in Example 2. After a total of 5 applications of the chemical plating agents to each sample, the samples were rinsed with tap water and blown dry. The metallic silver plated specimens were then placed into the molds, split rings secured into position on the plated dentin surfaces, and amalgam condensed onto the surfaces as described for Groups A and B. These samples were then stored in distilled water at 37° C. for further testing.

After all samples of Groups A, B, and C had been maintained in distilled water at 37° C. for 72 hours they were removed and tested as follows: The Teflon mold inserts were removed to expose the amalgam alloy cylinders or plugs which had been condensed onto the variously prepared dentin surfaces, each amalgam alloy plug extending generally perpendicular to the plane to which it was previously secured. The samples were mounted into test fixtures which held them securely in position. Each test fixture with sample in place was mounted on an Instron universal testing machine and a load applied parallel to the amalgam/dentin interface producing shear forces against the attached amalgam plug. The load was applied until the amalgam plug separated from the plated tooth specimen, and the force required to dislodge the amalgam recorded in pounds. The actual contact area of the amalgam/dentin interface was measured and the shear strength determined by dividing the maximum force recorded in pounds by the contact area. Shear strength is thus reported in pounds per square inch (psi). The results of this experiment is summarized below:

| Group | Treatment in Preparation for Amalgam | Average Shear Strength |
| --- | --- | --- |
| A | $H_3PO_4$ etched only | 0 (There was no adhesion of the amalgam to the dentin) |
| B | Etched as Group A plus $AgNO_3$ treated and photoreduced | 425 psi |
| C | Etched and photoreduced as in Group B plus chemical plating | 1200 psi |

EXAMPLE 4

Freshly-cut ivory slabs which had been stored continuously in distilled water were used to determine the efficiency of various combinations of light source and silver ion concentration of the photoreduction plating process. Ivory was used in this evaluation due to its similarity to human dentin, and homogeneity over a larger surface area as compared to an extracted tooth specimen.

The ivory slabs were acid etched using 37% phosphoric acid solution for one minute and then blown dry. Various photoreduction techniques were performed and evaluated. The following is a summary of the application technique and observed results:

A solution of 10% silver nitrate was swabbed onto the surface and then exposed to high intensity ultraviolet light for one minute. A non-homogeneous gray/black layer was obtained.

A 10% silver nitrate solution was applied to the etched ivory and exposed to high intensity ultraviolet light for five minutes. A homogeneous black photoreduced silver layer was obtained and microscopically measured to be 10-15 microns thick.

A 10% silver nitrate solution was applied to the etched ivory and exposed to high intensity ultraviolet light for 10 minutes. A homogeneous black layer 10-15 microns thick was obtained.

A 50% solution of silver nitrate was applied to the etched ivory surface and exposed to high intensity ultraviolet light for one minute. A homogeneous black photoreduced silver layer 10-15 microns thick was obtained.

A 50% solution of silver nitrate was applied to the etched ivory surface and exposed to high intensity ultraviolet light for five minutes. A homogeneous black layer 10-15 microns thick was obtained.

The previously-described five photoreduction techniques were repeated using high intensity visible light instead of the ultraviolet light source. The results obtained were identical to those observed using the ultraviolet light.

The conclusion drawn from this testing can be summarized as follows:

1. High-intensity visible light is equivalent to ultraviolet radiation for initiating the photoreduction of silver onto an ivory surface which has been etched for one minute using 37% phosphoric acid and then treated with silver nitrate solution.

2. A 10% solution of silver nitrate requires a minimum of five minutes of photoexposure to produce a homogeneous black layer 10-15 microns thick.

3. A 50% solution of silver nitrate requires a minimum of one minute photoexposure duration to produce a homogeneous black layer 10-15 microns thick.

4. A homogeneous black photoreduced silver layer of 10-15 microns is the maximum obtainable as longer photoexposure durations do not increase coating thickness.

EXAMPLE 5

The photoreduced silver plated ivory slabs described in Example 4 were subsequently chemically plated by the sequential application of 50% $AgNO_3$ solution and saturated $FeSO_4$ solution as described in Example 2. A total of five applications of the chemical plating were agents were applied to each sample and the coated samples were then cross-sectioned and examined microscopically to evaluate plating characteristics. The following observations were made:

1. A surface which had not been photoreduced and only had the chemical plating procedure was found to be non-homogeneous. A metallic layer with large silver crystals 80-90 microns thick was produced which was easily peeled off or wiped away using a cotton swab.

2. A surface which had been treated with the photoreduction step using 10% $AgNO_3$ and a photoexposure duration of five minutes, followed by the chemical plating step, produced a heavy, metallic, homogeneous, tightly-adhered silver coating 20-35 microns in thickness.

3. A surface which had been treated with the photoreduction step using 50% $AgNO_3$ and a photoexposure duration of one minute, followed by the chemical plating step, produced a heavy, metallic, homogeneous, tightly-adhered silver coating 20-35 microns in thickness.

4. A surface which had been treated with the photoreduction step, followed by chemical plating using 20% $AgNO_3$ and saturated $FeSO_4$ solution for a total of five applications, produced a heavy, metallic, homogeneous, tightly-adhered silver coating 25-35 microns in thickness.

EXAMPLE 6

A group of four freshly-extracted teeth were cut to remove the coronal enamel as in Example 1 and, after washing with distilled water and being blown dry with compressed air, were immediately treated as follows:

The teeth were etched for 60 seconds with 37% phosphoric acid solution, thereafter washed with tap water and blown dry. A silver fluoride solution, prepared by dissolving 1.0 gm of silver fluoride in 1.0 gm of distilled water, was applied to the tooth surfaces with a brush and the coating photoreduced for 60 seconds as in Example 1. The teeth were then washed with tap water and blown dry for visual examination. On observation, such teeth were found to have a gray to gray-black uneven, non-conductive surface coating. Such teeth were then chemically plated as in Example 2 except that the silver nitrate solution of the example was replaced by the saturated silver fluoride solution described.

After the teeth were chemically plated and blown dry they were again visually examined. All teeth were observed to have an uneven, non-homogeneous, semi-conductive gray to gray-black surface coating.

While in the foregoing we have disclosed an embodiment of this invention in considerable detail for purposes of illustration, it will be understood by those skilled in the art that many of these details may be varied without departing from the spirit and scope of the invention.

We claim:

1. A method for plating silver onto a dentin surface, comprising the steps of coating a dentin surface with an aqueous solution of a silver salt to produce a silver-protein complex upon said surface, photoreducing the silver of said complex to form a blackened discontinuous base layer of complexed metallic silver bonded to said surface, and thereafter electrolessly plating a continuous silver sealing layer upon said base layer by utilizing the silver of said silver-protein complex to catalyze the chemical reduction of the silver ions of said plating solution.

2. The method of claim 1 in which there are the further steps of acid etching said dentin surface, and then washing the etchant from said surface, prior to said coating step.

3. The method of claim 2 in which said acid etching step comprises treating said dentin surface with a non-toxic acid selected from the group consisting of phosphoric and nitric acids.

4. The method of claim 2 in which said acid treating step comprises treating said dentin surface with an aqueous solution of phosphoric acid.

5. The method of claim 1 in which there is the additional step of applying and adhering a tooth restorative material to said continuous silver layer.

6. The method of claim 5 in which said restorative material is silver amalgam.

7. The method of claim 1 in which said photoreduction step includes directing high intensity artificial light towards the coated surface for an interval of about 0.5 to 5 minutes.

8. The method of claim 1 in which said plating step includes contacting the dentin surface following said photoreduction with an aqueous plating mixture containing a water soluble silver salt and a reducing agent for the silver ions of said salt.

9. The method of claim 8 in which said silver salt is selected from the group consisting of silver nitrate and silver fluoride.

10. The method of claim 9 in which said silver salt is silver nitrate and said reducing agent is selected from the group consisting of ferrous sulfate, ferrous ammonium sulfate, formaldehyde, hydrazine, dimethylaminoborane, alkali metal formates, and alkali metal hypophosphates.

11. The method of claims 9 or 10 in which said reducing agent is ferrous sulfate.

12. The method of claims 9 or 10 in which said reducing agent is ferrous ammonium sulfate.

13. A method for plating a metal onto a dentin surface, comprising the steps of coating the dentin surface with an aqueous solution containing a salt of the metal, photoreducing the aqueous solution to form a base layer consisting essentially of a complex of the metal bonded to the surface, and thereafter electroless plating a second layer of the metal upon the base layer by reducing ions of the metal, and utilizing the metal of said base layer to catalyze the reduction of the metal ions in the second layer.

* * * * *